US006352834B1

(12) United States Patent
Dreicer et al.

(10) Patent No.: US 6,352,834 B1
(45) Date of Patent: Mar. 5, 2002

(54) PROSTATE CANCER ASSAYS AND RELATED METHODS

(75) Inventors: Robert Dreicer; John Kemp, both of Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 09/118,222

(22) Filed: Jul. 17, 1998

(51) Int. Cl.[7] .............................................. G01N 33/53
(52) U.S. Cl. .................... 435/7.23; 530/387.1; 435/7.1; 435/7.93; 435/7.94; 435/7.95; 435/962
(58) Field of Search ................................ 435/7.1, 7.23, 435/7.93, 7.94, 7.95, 962; 530/387.1

(56) References Cited

U.S. PATENT DOCUMENTS

| RE33,405 E | 10/1990 | Chu et al. ................... 435/7.23 |
| 5,599,677 A | * 2/1997 | Dowell et al. ................ 435/7.4 |
| 5,614,372 A | 3/1997 | Lilja et al. .................. 435/7.23 |
| 5,688,658 A | 11/1997 | Diamandis ................. 435/7.23 |

OTHER PUBLICATIONS

Dreicer R et al. Cancer Invest 15 (4):311–317), 1997.*
Kantoff, P.W. et al. Hautolopy/Oncology Clinics of North America, 8(3):555–572,1994.*
Hallaway, et al, 86 *Proc Nat'l Acad Sci USA* 10108 (1989).
Kemp, et al, 55 *Can Res* 3817 (1995).
Kovar, et al, 63 *Pathobiology* 65 (1995).
Kovar, et al, 65 *Pathobiology* 61 (1997).
Forsbeck, et al, 37 *Scand J Haematol* 429 (1986).
Carpino, et al, 105(3) *Experimental & Clinical Endocrinology and Diabetes* 169 (1997).
Picurelli, et al., 9(1) *Trace Elem. Med.* 14 (1992).

* cited by examiner

*Primary Examiner*—Susan Ungar
*Assistant Examiner*—Minh-Tam Davis
(74) *Attorney, Agent, or Firm*—Schwegman, Lundberg, Woessner & Kluth, P.A.

(57) ABSTRACT

The present invention includes a method for stimulating increased PSA production by prostate cancer cells, comprising the steps of reducing the amount of iron available to the prostate cancer cells; and causing increased PSA production. In another aspects of the present invention, there are provided prostate cancer diagnostic kits comprising a first container containing an iron chelator; and second container containing a free-PSA-specific antibody, wherein the free-PSA-specific antibody is detectable. Also provided as part of the present invention are methods for diagnosing prostate cancer in a human, comprising reducing the amount of available iron in the human, and subsequently testing PSA levels.

6 Claims, No Drawings

PROSTATE CANCER ASSAYS AND RELATED METHODS

The research leading to this invention was funded by the U.S. Government; the U.S. Government may have certain rights in this invention.

BACKGROUND OF THE INVENTION

In 1995, an estimated 41,000 deaths from metastatic prostate cancer occurred, despite some promising treatments. Some of these deaths would have been prevented had prostate specific antigen diagnostic tests been more reliable. The present invention improves the specificity of PSA screening tests, and will increase survival rates via early detection and early treatment.

Great strides have been made in detection of prostate malignancies since the identification of prostate specific antigen (PSA) by Wang et al. in 17 *Invest Urol* 159 (1979), the subject matter of which was claimed in U.S. Pat. No. 4,446,122 (reissued as Reissue No. 33,405 in 1990). Distinctions can now be made between patients whose PSA levels are elevated due to prostate cancer and those whose PSA levels are elevated due to benign prostate hypertrophy. For example, U.S. Pat. No. 5,614,372 and U.S. Pat. No. 5,599,677 describe some of the strategies used to distinguish the two forms. These three patents (U.S. Pat. No. 4,446,122, including Re. 33,405, U.S. Pat. No. 5,614,372 and U.S. Pat. No. 5,599,677) are hereby incorporated by reference in their entirety into this application. In particular, U.S. Pat. No. 5,599,677 at column 2, lines 1–13 discusses PCT patent application WO 92/01936. WO 92/01936 is incorporated by reference into U.S. Pat. No. 5,599,677 (see, colunmn 15, lines 51–54). Table 2a, found at page 12 of WO 92/01936 presents the results of the testing of patient samples for free, complexed and total PSA. In the table, BPH indicates benign prostatic hyperplasia, CAP indicates prostate cancer, G indicates the differentiation grade, and T indicates the grade. Table 2a is reproduced below:

TABLE 2a

|  |  | Correlation coefficient | Ratio mean |
|---|---|---|---|
| BPH (n = 144) | A. PSA c/PSA tot | 0.932 | 0.970 |
|  | B. PSA f/PSA tot | 0.853 | 0.302 |
| CAP (n = 122) | A. | 0.994 | 1.219 |
|  | B. | 0.784 | 0.191 |
| CAP, G1 (n = 31) | A. | 0.994 | 1.628 |
|  | B. | 0.922 | 0.190 |
| CAP, G2 (n = 47) | A. | 0.972 | 1.141 |
|  | B. | 0.956 | 0.169 |
| CAP, G3 (n = 43) | A. | 0.996 | 1.014 |
|  | B. | 0.818 | 0.218 |
| CAP T1-2 (n = 56) | A. | 0.985 | 1.044 |
|  | B. | 0.868 | 0.178 |
| CAP T3-4 (n = 65) | A. | 0.993 | 1.372 |
|  | B. | 0.770 | 0.204 |
| CAP T4 (n = 25) | A. | 0.997 | 1.174 |
| (not treated) | B. | 0.825 | 0.188 |
| BPH (n = 84) PSA ≦ 5 | A. | 0.879 | 1.059 |
|  | B. | 0.850 | 0.301 |
| BPH (n = 60) PSA > 5 | A. | 0.888 | 0.846 |
|  | B. | 0.735 | 0.303 |
| CAP (n = 26) PSA ≦ 5 | A. | 0.913 | 1.773 |
|  | B. | 0.826 | 0.202 |
| CAP (n = 94) PSA >5 | A. | 0.993 | 1.065 |
|  | B. | 0.778 | 0.188 |
| CAP (n = 25) | A. | 0.919 | 1.025 |

TABLE 2a-continued

|  |  | Correlation coefficient | Ratio mean |
|---|---|---|---|
| PSA > 5 ≦ 20 | B. | 0.502 | 0.187 |
| CAP (n = 69) | A. | 0.993 | 1.080 |
| PSA > 20 | B. | 0.770 | 0.184 |

Commercially-available PSA assays are commonly sold as kits, and the assays performed in regional or local laboratories. For example, PSA diagnostic kits are sold under the names of: PROS-CHECK PSA, from Yang Laboratories, Inc. Bellevue, Wash.; Hybritech Tandem-E and Hybritech Tandem-R, from Hybritech, Inc., La Jolla, Calif.; Abbott Imx PSA Assay, from Abbott Laboratories, Abbott Park, Ill.; and ACS PSA Assay, from Ciba-Corning Diagnostics Corporation, East Walpole, Mass.

These kits (and other assays, for example, those mentioned in U.S. Pat. Ser. No. 5,688,658) play a critical part of the current strategy for early detection of prostate cancer. A problem arises, however, when a modestly abnormal PSA value (4–10 ng/ml) is encountered in the context of a negative digital rectal exam (DRE). Only 20–30% of individuals with such findings will demonstrate carcinoma on biopsy (Kantoff and Talcott, 8(3) *HematollOncol Clinics N Amer* 555 (1994)). It has therefore been important to develop strategies that increase the positive predictive value of PSA testing. Such strategies now include establishing age-adjusted normal ranges, determining the free to total PSA ratio, correcting for prostate gland mass (density), and calculating the rate of change of PSA values (Kantoff and Talcott, 8(3) *Hematol.Oncol Clinics N Amer* 555 (1994) and Brawer, 45 *CA-A Cancer J Clinicians* 148 (1995)). While each of these strategies has made a contribution, considerable uncertainty nevertheless remains about how to proceed with a patient who is PSA positive and DRE negative.

The present invention provides hope for those patients who have modestly elevated PSA levels, in that additional procedures may be avoided (such as biopsy) or treatment may be initiated earlier in the disease progession. One aspect of the present invention is the effective reduction of available intracellular iron in prostate carcinoma cells prior to administration of a PSA diagnostic test. Most information describing the interaction between iron levels and cancer has been generated in the context of therapeutics, however, and not diagnostics.

Iron is a key nutrient in mammalian health; iron is necessary in proper hemoglobin structure and function (hemoglobin is the primary component of red blood cells), DNA synthesis, and energy transport. In the body, iron is absorbed from food or supplements in the intestine, and transported via the blood to cells by an appropriately-named protein called "transferrin". Receptors on the cell's surface recognize and bind the iron-carrying transferrin and the iron is then made available to the cell's interior. In certain situations, however, it has been shown to be therapeutically desirable to purposely cause a state of partial iron deficiency.

For example, three types of iron deprivation cancer treatment are currently under study. Deferoxamine (called "DFO" in this application, but also referred to as desferi-oxamine in the art) is the first treatment, and it is being investigated in the treatment of neuroblastoma (Donfrancesco et al., 4 *Anti-Cancer Drugs* 317 (1993)) and hepatoma (Kountouras et al., 42 *Hepato-gastroenterol* 31 (1995). The second treatment, gallium nitrate, is being investigated in transitional cell carcinoma (Seligman and Crawford, 83(21) *J Nat Cancer Inst* 1582 (1991) and lymphoma (Chitambar et al., 20(2) *Am J Clin Oncol* 173 (1997)). The third treatment involves the use of monoclonal antibodies against the transferrin receptor. These antibodies have shown promise against lymphomas in animal models (White et al., 50 *Can Res* 6295 (1990) and Kemp et al., 55 *Can Res* 3817 (1995)) and in a Phase I clinical trial (Brooks et al., 1 *Clin Cancer Res* 1259 (1995). It is now clear that all three forms of treatment, and iron deprivation per se, can induce apoptosis (Ul-Haq et al., 23 *Exp Hematol* 428 (1995); Hileti et al., 89 *Br J of Haematol* 181 (1995); Fukuchi et al., 350 *FEBS Letters* 139 (1994); Kovar et al., Abstract 38C13 in 65 *Pathobiology* 61 (1997).

In related research, iron appears to be a growth factor for tumor cells that metastasize to bone (Rossi and Zetter, 89 *Proc Natl Acad Sci USA* 6197 (1992). In addition, one effect of suramin (an agent that is active against prostate cancer) is to partially inhibit the binding of transferrin to its receptor (Forsbeck et al., 37 *Scand JHaematol* 429 (1986). Moreover, the present inventors found that combined iron deprivation/ monoclonal antibody treatment produced significant inhibition of growth of prostate carcinoma cell lines in vitro (Kovar et al., 63 *Pathobiology* 65 (1995). These results then led to a Phase II trial of DFO as a single agent against disseminated prostate cancer (Dreicer et al., 15(4) *Cancer Investigation* 311 (1997). In that trial, prostate cancer patients were given consecutive eight hour intravenous infusions of DFO. The DFO treatment was associated with rising PSA levels in eight out of nine patients, even though their disease appeared to be stable by clinical criteria.

The result in Dreicer et al. was contrary to numerous studies which indicated that rising PSA levels indicate recurrent or residual disease. Brawer et al., 33 (5 supp) *Urology* 11 (1989); Siddal et al., 12 *Eur Uro* 1 (1986); Starney et al., 317 *N Eng J Med* 909 (1987); Lange et al., 141 *J Urol* 873 (1989); Starney et al., 141 *J Urol* 1076 (1989) Starney et al., 141 *J Urol* 1088 (1989) and Chan et al., 33 *Clin Chem* 1916 (1987).

Additionally, recent research has resulted in the production of a high molecular weight hydroxyethylstarch conjugate form of deferoxamine called HES-DFO (Hallaway et al., 86 *Proc Natl Acad Sci USA* 10108 (1989). HES-DFO has a better toxicity profile than the common mesylate salt form of DFO (ibid.). HES-DFO has been used in pre-clinical studies of combination iron deprivation treatment in a murine lymphoma model (Kemp et al., 55 *Can Res* 3817 (1995)).

Lastly, in a recent study of seminal plasma samples from patients with thalassemia, Carpino et al. noted that patients with high serum ferritin levels exhibited decreased PSA levels (Carpino et al., 105(3) *Exp Clin Endocrin and Diabetes* 169 (1997)).

Citation of the above documents is not intended as an admission that any of the foregoing is pertinent prior art. All statements as to the date or representation as to the contents of these documents is based on subjective characterization of information available to the applicant, and does not constitute any admission as to the accuracy of the dates or contents of these documents.

SUMMARY OF THE INVENTION

The present invention provides a strategy for increasing the specificity and predictive value of PSA testing. The use of this strategy will result in more prostate cancers being detected earlier and the number of unnecessary prostate biopsies being decreased.

It is therefore an object of the present invention to provide a method to stimulate prostate specific antigen (PSA) production by prostate carcinoma cells.

Specifically, it is an object to provide a method to stimulate prostate specific antigen (PSA) production by prostate carcinoma cells by exposing such tumor cells to an iron chelator.

It is a further object to provide a method for increasing PSA levels in a patient who has undiagnosed prostate cancer by administering an iron chelator and subsequently testing PSA levels.

Definitions (for the purposes of the present application, the following terms shall have the following meanings):

Bioavailable iron shall mean unchelated iron.

DETAILED DESCRIPTION OF THE INVENTION

The present invention includes a method for stimulating increased PSA production by prostate cancer cells, comprising the steps of reducing the amount of bioavailable iron in prostate cancer cells; and thus causing increased PSA production. Preferably, the method is one wherein the prostate cancer cells are in situ or in vivo.

In one aspect of the present invention, the amount of bioavailable iron in the prostate cancer cells is reduced by means of an iron chelator. In this aspect, the preferable iron chelator is either DFO or HES-DFO. A method wherein the iron chelator is administered via a single bolus injection is most preferred.

In conjunction with the method for stimulating increased PSA production by prostate cancer cells, it is desirable to add the step of quantifying the increased PSA. Preferred means for quantification of PSA is through the use of a commercially-available PSA diagnostic kit, such as: PROS-CHECK PSA; Hybritech Tandem-E; Hybritech Tandem-R; Abbott Imx PSA Assay; and ACS PSA Assay.

Iron may be reduced by any conventional iron-reduction protocol, or by any protocols developed in the future. Essentially, the iron ought to be a) reduced in amount or b) reduced in activity. In other words, some iron needs to be eliminated from the system, or the iron that is in the system needs to be rendered inactive.

To reduce the available iron, one can administer a compound that binds to the iron cations and reduces their ability to affect other materials. Such a compound can temporarily bind the iron cations, and thereby reduce the amount of time the iron is available in the system, or permanently bind the iron cations, and render them unavailable for futher chemical reactions.

One class of compounds that are particularly useful for reducing the amount of available iron are the iron chelators. These compounds are generally competitive binders of ferric iron ($Fe3+$) which is normally stored within the cell by ferritin.

Deferoxamine and HES-deferoxamine are examples of iron chelators. Other examples are: 1-2 dimethyl-3-hydroxypyrid-4-one (also known as L-1, deferiprone and CP20); N, N-bis(2-hydroxybenzyl)ethylenediamine-N,N-diacetic acid (HBED); desferrithiocin; phytic acid; pyridoxal isonicotinoyl hydrazone (PIH) or any analogues of the compounds in this list. Bacterial iron chelators such as parabactin and vibriobactin are also within the scope of the present invention. Information regarding these compounds is available through the National Institutes of Health's PubMed database at www.ncbi.nlm.nih.gov/PubMed/.

For prostate cancer cells in situ, the levels of iron available to prostate cancer cells can be lowered so much that DNA synthesis is inhibited. These significantly-altered levels can be achieved using any known method or any method available in the future. Use of iron chelators is particularly effective. Iron chelators can be administered via any medically-acceptable method, although the oral, intravenous and subcutaneous routes are preferred.

The formulation of the iron chelators can be any iron reducing formulation. Any salt form is acceptable, so long as it meets the iron reducing requirement, and any buffer or conjugate is acceptable as well, so long as an ability to reduce available iron is present in the final form. Preferred salt forms are those which are pharmaceutically-acceptable, such as DFO mesylate. Preferred buffers are any which are pharmaceutically-acceptable, such as normal saline. Other preferred aspects of an iron chelator formulation are polymers which improve the function of known chelators, an example of which is HES-DFO.

DFO may be obtained through commercial sources or manufactured de novo, according to a process known in the art. The commercial source of DFO is Novartis (East Hanover, N.J.). DFO may further be altered for a certain purpose according to methods known in the art, especially with regard to pharmaceutical formulations.

The preferred dose of DFO is 50 mg/kg/day, parenterally, with determination of PSA increase on Day 6. However, any dosage and regimen which results in elevated PSA levels is within the scope of the present invention.

HES-DFO may be obtained through commercial sources or manufactured de novo, according to a process known in the art. The commercial source of HES-DFO is Biomedical Frontiers, Minneapolis, Minn. Moreover, HES-DFO can be manufactured de novo according to U.S. Pat. Ser. Nos. 4,863,964 and 5,217,998, which patents are hereby incorporated by reference into this application. HES-DFO may further be altered for a certain purpose according to methods known in the art, especially with regard to pharmaceutical formulations.

The preferred dose of HES-DFO is 25–150 mg/kg, via single bolus injection 96 hours prior to determination of PSA increase. A preferred dose is 50 mg/kg.

Despite the preferred embodiments described above, the iron chelator(s) can be administered at any time which allows increased PSA levels, in the event that prostate cancer is present in the subject. Preferably, the iron chelators are administered approximately 96 to 120 hours before the time PSA levels are to be identified. More preferred is a method wherein the iron chelators are administered approximately 96 hours before the time PSA levels are to be identified. Of course, the dosage can be tailored to suit the timing of the PSA test. For instance, a higher dose can be given in anticipation of a shorter time between the dosing and the test. A lower dose can be given in anticipation of a longer time between the dosing and the test. Multiple dosings may also be given as needed. The PSA levels will be altered in response to the dosage and timing.

Quantification of PSA levels may be accomplished according to any known procedure, or any procedure developed in the future. In general terms, the known PSA tests share the following steps: first, a sample (generally a biological sample, such as blood, serum, plasma, prostatic fluid, seminal fluid, urine, lymph or spinal fluid) is taken; second, PSA (sometimes particular forms of PSA) amount is determined. The following assays are commercially-available, and more are mentioned at U.S. Pat. Ser. No. 5,599,677, which patent has been incorporated by reference: PROS-CHECK PSA, from Yang Laboratories, Inc. Bellevue, Wash.; Hybritech Tandem-E and Hybritech Tandem-R, from Hybritech, Inc., La Jolla, Calif.; Abbott Imx PSA Assay, from Abbott Laboratories, Abbott Park, Ill.; and ACS PSA Assay, from Ciba-Corning Diagnostics Corporation, East Walpole, Mass. These kits have instructions as part of the packaging, and, for the purposes of the present invention, no refinement of the kit instructions are necessary, even though those in the art are aware of certain modifications that can enhance the assays' accuracy or precision.

In another aspects of the present invention, there are provided prostate cancer diagnostic kits comprising a first container containing an iron chelator; and second container containing a free-PSA-specific antibody, wherein the free-PSA-specific antibody is detectable. Preferrably, the free-PSA-specific antibody is detectable via a label or via a labeled antibody. In another embodiment, the kits of the present invention can comprise a third container containing a detectable antibody specific for any PSA, so as to allow comparison between free PSA levels and total levels.

Specifically, the preferred kits of the present invention comprise (a) a first container containing an iron chelator; and a commercial PSA assay kit selected from the group consisting of: PROS-CHECK PSA; Hybritech Tandem-E; Hybritech Tandem-R; Abbott Imx PSA Assay; and ACS PSA Assay.

The iron chelator in the present kits can be any iron chelator. Preferred kits contain DFO or HES-DFO in sterile solution, or a combination of both. However, a kit that contains powdered iron chelate with the appropriate amount of buffered sterile water in a separate container is also within the scope of the present invention. The kit can contain appliances needed to administer such iron chelator, for instance, a sterile syringe and needle. The amount in kit can be more than typically needed for the heaviest people, since all need not be used. For instance, a very heavy person of 300 pounds would typically require approximately 7 grams molar equivalent of iron chelator to produce the desired result. Therefore, the kits can contain this amount, and if the entire amount is not used, say for a lighter person, then the remainder can be thrown away. However, it is also possible to provide varying amounts of iron chelator, for varying people. If the iron chelator is provided in solution, then the container holding it is preferably a puncture resistant one (with the exception of a needle-puncturable section for delivery into the syringe) and either rigid or flexible.

In the present kit, PSA can be detectable by any means, ie. enzyme immunoassay, radioimmunoassay (competitive or non-competitive, including MONO and MOLY sandwich assays), chemi- or bio-luminescent assay, fluroescent immunoassay and DNA based assays (ie. PCR amplification). Particular assays are: resolved immunofluorometry (as in U.S. Pat. Ser. No. 5,688,658, which patent is expressly incorporated by reference in its entirety into this application); chemiluminescence with acridinium esters as labels, enzumatically triggered chemiluminescence with alkaline phosphatase and by horseradish peroxidase; immunoassays using alkaline phosphatase and the fluorogentic substrate 4-methylumbelliferyl phosphate or p-nitrophenyl phosphate, immunoassay using horseradish peroxidase and substrates like ABTS and teramethylbenzidine and time-resolved immunoflurorometric assays with Bu3+. U.S. Pat. No. 5599677 describes immunoassays for prostate specific antigen and Kuriyama et al., 40 Cancer Res. 4658 (1980) describes an enzyme immunoassay which made it possible to detect low concentrations of PSA in the blood of patients with malignant and benign prostate disease.

The free-PSA-specific antibody can be alpha HE, According to U.S. Pat. No. 5,599,677 or others. CanAg Diagnostics AB, Gothenburg, Sweden sell at least 9 major antigenic determinants on the PSA molecule, and other PSA-specific antibodies are characterized in the patent applications which have been incorporated by reference into this application.

Optimally, the present kits include an iron chelator in a container and the materials from commercially-available kits, such as those materials found in PROS-CHECK PSA, from Yang Laboratories, Inc. Bellevue, Wash.; Hybritech Tandem-E and Hybritech Tandem-R, from Hybritech, Inc., La Jolla, Calif.; Abbott Imx PSA Assay, from Abbott Laboratories, Abbott Park, Ill.; and ACS PSA Assay, from Ciba-Corning Diagnostics Corporation, East Walpole, Mass.

Lastly, written instructions can also be included in kit of the present invention. Such instructions would included dosage and administration information, as well as contraindications. Information on quantification, such as protocols to follow, and interpretation of results would also be included.

Also provided as part of the present invention are methods for diagnosing prostate cancer in a human, comprising reducing the amount of available iron in the human, and subsequently testing PSA levels. A preferred method of this type is one wherein the amount of available iron is reduced by means of an iron chelator. In this embodiment, the iron chelator is preferably DFO or HES-DFO. The additional step of comparing the level of free PSA to bound PSA is also contemplated as within the present method.

Most preferred is a method for diagnosing prostate cancer in a human, comprising reducing the amount of available iron in the human, and subsequently testing PSA levels via the instructions in a commercially available kit, such kit selected from the group consisting of: PROS-CHECK PSA; Hybritech Tandem-E; Hybritech Tandem-R; Abbott Imx PSA Assay; and ACS PSA Assay.

Although, for the most part, PSA assays are indicated for human males at risk of prostate cancer, the present method is not limited to human males. For example, U.S. Pat. Ser. No. 5,688,658 discloses the use of PSA as a marker for breast cancer, and the present invention therefore extends its usefulness to human females as well. Diagnosis of prostate or breast cancer in livestock or companion animals is also within the scope of the present invention. However, the best mode contemplated at the time of filing the present invention is for the use of iron chelators in human males prior to a PSA test.

DFO and HES-DFO may be obtained as described above and formulated according to known and described parameters. Moreover, administration of the iron chelators are according to any medically-acceptable method, especially in the dosage forms, amounts and time periods described above for the use of such chelators in a kit Quantification of PSA levels may be accomplished according to procedure described above as well.

EXAMPLES

Example 1

In a group of experiments in which LNCaP cells were cultured for 72 hours with varying doses of DFO mesylate (Desferal), PSA assays performed on the tissue culture supernatants indicated that production of PSA per viable cell rose by 33.6% under conditions which resulted in slight slowing of growth but which did not produce any significant change in overall cell viability (Table 2).

TABLE 2

PSA produced by LNCaP after culture with Desferal for 72 Hrs.

| Condition | Total Cells $\times 10^6$ | Total Viable Cells $\times 10^6$ | Total PSA (ng)* | % Inhibition 3H | % Viability | Molecules PSA Per Cell $\times 10^{7}$** | Molecules PSA Per Viable Cell $\times 10^7$ |
|---|---|---|---|---|---|---|---|
| Media | — | — | 0 | — | — | — | — |
| Untreated | 1.16 | 1.15 | 672 | — | 93.9 | 1.06 | 1.13 |
| Desferal 0.1 ug/ml | 1.09 | 1.01 | 710 | 1.8 | 93.0 | 1.20 | 1.28 |
| Desferal 0.25 ug/ml | 1.07 | 1.00 | 710 | 6.8 | 93.8 | 1.22 | 1.30 |
| Desferal 0.50 ug/ml | 1.13 | 1.06 | 650 | 7.4 | 93.4 | 1.06 | 1.14 |
| Desferal 1.0 ug/ml | 1.14 | 1.05 | 644 | 10.6 | 92.2 | 1.04 | 1.12 |
| Desferal 2.0 ug/ml | .900 | 840 | 642 | 21.1 | 98.3 | 1.32 | 1.41 |
| Desferal 2.5 ug/ml | .810 | .760 | 627 | 26.8 | 94.3 | 1.42 | 1.51 |
| Desferal 3.0 ug/ml | .744 | .680 | 587 | 40.3 | 90.9 | 1.45 | 1.59 |
| Desferal 4.0 ug/ml | .730 | .620 | 611 | 52.7 | 85.4 | 1.54 | 1.80 |

*From 3.0 milliliters of collected supernatant per well.
**PSA per cell using total cells recovered.

Comment: Table 2 is data from one of three similar experiments in which cells were cultured for 72 hours following the methods described in the proposal (i.e., cells in 6-well plates for PSA studies and cells in 96-well plates for thymidine incorporation, both at the same cell concentration). Note that as DFO dose rises a dose dependent effect becomes apparent and that at a dose 2.5 micrograms/ml of DFO, there is a slowing of growth (26.8% inhibition of thymidine incorporation–column 5) but no loss of viability (column 6). For viable cells, the per cell production of PSA rose 33.6% (column 8: PSA value of 1.5×10E7 molecules per cell divided by control value of 1.13×10E7).

Example 2

LNCaP cells were cultured for 96 hours (rather than 72) in the presence of varying doses of HES-DFO rather than DFO mesylate. In that experiment, PSA production per viable cell rose by 54% under conditions which produced slight slowing of growth (9.5%) and no effect on viability. Moreover, PSA production rose by 90% under conditions which produced partial growth inhibition (39%) and only a slight (3%) decline in overall cell viability (Table 3).

TABLE 3

PSA produced by LNCaP after culture with HES-DFO for 96 Hrs.

| Condition | Total Cells × $10^6$ | Total Viable Cells × $10^6$ | Total PSA ug/ml | % Inhibition (3H) | % Viability | Molecules Per Cell × $10^6$ (all cells) | Molecules Per Cell × $10^6$ (viable cells) |
|---|---|---|---|---|---|---|---|
| Untreated | .791 | .767 | 70.8 | — | 97.0 | 4.77 | 4.91 |
| HES-DFO 5 ug/ml | .731 | .700 | 74.5 | 0.8 | 95.7 | 5.42 | 5.61 |
| HES-DFO 10 ug/ml | .749 | .700 | 73.7 | 0.0 | 93.5 | 5.24 | 5.60 |
| HES-DFO 15 ug/ml | .525 | .504 | 71.4 | 9.5 | 96.1 | 7.26 | 7.55 |
| HES-DFO 25 ug/ml | .483 | .455 | 80.0 | 39.1 | 94.2 | 8.79 | 9.33 |
| HES-DFO 35 ug/ml | .525 | .480 | 69.7 | 71.7 | 91.4 | 7.33 | 7.71 |
| HES-DFO 45 ug/ml | .361 | .298 | 70.3 | 86.1 | 82.7 | 10.38 | 12.54 |
| HES-DFO 55 ug/ml | .488 | .399 | 64.2 | 93.0 | 89.3 | 7.42 | 8.55 |

Comment: Table 3 is data from a single experiment with HES-DFO and LNCaP for a culture period of 96 hours rather than 72. All of the data are shown. The control was performed in quadruplicate and each of the HES-DFO dose groups in duplicate. Note that at a HES-DFO dose of 15 micrograms/ml, PSA production per viable cell (column 8) is increased by 54% compared to the control (average of 8.1 and 6.99=7.55, average for control=4.91; 7.55/4.91=1.54) while viability remains unaffected (column 6). At 25 micrograms/ml, there is some (39.1%) inhibition of cell growth and a slight (2–3%) decline in viability, but PSA production has risen by 90% (average of 8.97 and 9.69= 9.33; 9.33/4.91=1.90). The relative ratio of the dose of HES-DFO required to produce an effect equivalent to that for a given dose of DFO is consistent with our prior work (6).

The tissue culture studies show that deferoxamine-induced iron deprivation results in increased PSA secretion per cell. They also point toward the use of LNCaP as a convenient model for further experimentation in vivo in nude mice.

Although the present invention has been fully described herein, it is to be noted that various changes and modifications are apparent to those skilled in the art. Such changes and modifications are to be understood as included within the scope of the present invention as defined by the appended claims.

What is claimed is:

1. A method for diagnosing prostate cancer in a human, comprising the steps of
   (a) determining an initial total prostate specific antigen (PSA) level present in the human,
   (b) reducing the amount of available iron in the human,
   (c) determining a post iron treatment total prostate specific antigen level in the human, and
   (d) comparing the initial and post iron treatment total PSA level,
   wherein an increase between the initial and post iron treatment total PSA level is indicative of prostate cancer in the human.

2. A method of claim 1, wherein the amount of available iron is reduced by means of an iron chelator.

3. A method of claim 1, wherein the iron chelator is deferoxamine.

4. A method of claim 2, wherein the iron chelator is HES-deferoxamine.

5. A method of claim 1, which further comprises comparing the level of free prostate specific antigen to total prostate specific antigen in step (a) to yield an initial free-PSA:total PSA ratio and a post iron treatment free-PSA:total PSA ratio, wherein a decrease in the ratio is indicative of the presence of prostate cancer.

6. A method of claim 5, wherein the prostate specific antigen levels are tested according to the instructions in a prostate specific antigen diagnostic kit.

* * * * *